United States Patent
Choate

(10) Patent No.: US 6,179,439 B1
(45) Date of Patent: *Jan. 30, 2001

(54) HIGH-INCIDENCE PROGRAMMABLE SURFACE ILLUMINATOR FOR VIDEO INSPECTION SYSTEMS

(75) Inventor: Albert G. Choate, Rush, NY (US)

(73) Assignee: Optical Gaging Products, Inc., Rochester, NY (US)

( * ) Notice: Under 35 U.S.C. 154(b), the term of this patent shall be extended for 0 days.

This patent is subject to a terminal disclaimer.

(21) Appl. No.: 09/095,060

(22) Filed: Jun. 10, 1998

(51) Int. Cl.$^7$ ....................................... F21V 7/00
(52) U.S. Cl. .................. 362/247; 362/244; 362/251; 362/800; 359/387; 359/388
(58) Field of Search .................... 362/247, 251, 362/364, 311, 444, 455, 244, 800; 359/355, 387, 388

(56) References Cited

U.S. PATENT DOCUMENTS 4,475,796 * 10/1984 Kimura ................................ 350/525
4,985,814 * 1/1991 Lyons ................................... 362/240
5,690,417 * 11/1997 Polidor et al. ....................... 362/244

* cited by examiner

Primary Examiner—Sandra O'Shea
Assistant Examiner—John Anthony Ward
(74) Attorney, Agent, or Firm—Shlesinger, Fitzsimmons & Shlesinger

(57) ABSTRACT

A lens housing has an axial bore containing a lens system for projecting through the bore the image of an illuminated object which is located beyond one end of the lens housing. The lens housing is surrounded by a lamp housing which contains a plurality of spaced lamps that are operable to direct spaced, parallel, collimated beams of light through an open end of the lamp housing, and toward the object that is to be illuminated. A paraboiloidal or ellipsoidal reflector, which is interposed between the lamp housing and the object, has in one end thereof a relatively large diameter opening which is releasably secured over the open end of the housing, and has in its opposite end a smaller opening registering with, and for accommodating a portion of the object that is to be illuminated. The collimated light beams are directed by the reflector onto the portion of the object at angles of incidence in the range of 40° to in excess of 90°.

14 Claims, 3 Drawing Sheets

HIGH-INCIDENCE PROGRAMMABLE SURFACE ILLUMINATOR FOR VIDEO INSPECTION SYSTEMS

BACKGROUND OF THE INVENTION

This invention relates to surface illuminators of the type employed with video inspection systems, and more particularly to an improved, high-incidence programmable surface illuminator capable of directing collimated light beams onto an inspected workpiece at angles of incidence in the range of approximately 45° to beyond 90°.

Heretofore a variety of systems have been developed for illuminating and inspecting workpieces or manufactured parts of various shapes and configurations. Such devices, frequently referred to as surface illuminators, frequently are designed so that the part that is to be inspected is surrounded by one or more light sources which direct illumination obliquely onto the surface or surfaces of the part to be inspected. U.S. Pat. No. 4,893,223, for example, utilizes a plurality of light emitting diodes that are mounted in locations disposed in a segmental spherical array, so that light beams therefrom are directed at different angles of incidence onto the surface of the part to be inspected. A somewhat similar illuminating system is disclosed in U.S. Pat. No. 5,038,258, in which case light modulators are interposed between the sources of light and the part that is being inspected. Moreover, in U.S. Pat. No. 5,690,417, which is owned by the same assignee as the present application, a plurality of light sources in the form of light emitting diodes, or the like are arranged in radially spaced, circular arrays between a Fresnel lens and a workpiece that is to be inspected. As a consequence, collimated beams of light are directed by the Fresnel lens obliquely, and at different angles of incidence onto the part that is being inspected.

While the foregoing illuminator devices are suitable for inspecting certain types of workrjieces, it has been found that there is a need for a surface illuminator which can direct beams of light from an LED array toward a common focus located at the part that is to be inspected, and in such manner that the beams of light are directed at angles of incidence encompassing a range not heretofore possible by prior art devices—namely, providing angles of incidence that range from around 45° to beyond 90°.

Accordingly, it is an object of this invention to provide an improved high-incidence, programmable surface illuminator which is capable of directing onto a part that is to be inspected an array of collimated light beams which can be directed onto the workpiece at angles of incidence ranging from around 45° to beyond 90°.

A further object of this invention is to provide a surface illuminator of the type described in which an ellipsoidal or concave paraboloidal mirror is utilized to reflect beams of light from an array thereof to a common object plane or focus, and at angles of incidence ranging from around 45° to beyond 90°.

Still a further object of this invention is to provide an improved surface illuminator of the type described in which the paraboloidal mirror and object being inspected are capable of being adjusted relative to each other, thereby to alter the range of angles of incidence of the beams that are directed onto the workpiece.

Other objects of the invention will be apparent hereinafter from the specification and from the recital of the appended claims, particularly when read in conjunction with the accompanying drawings.

SUMMARY OF THE INVENTION

A generally disc-shaped lamp housing has secured therein a plurality of spaced, parallel, light emitting lamps or diodes the axes of which extend parallel to and are radially spaced from the axial centerline of the housing. Moreover, the light emitting ends of the lamps face in the same direction (downwardly in the embodiment illustrated) and direct their beams of light onto a paraboloidal shaped reflective surface such as formed by the inside surface of a reflector or mirror which is secured coaxially over the lower end of the housing. The lamps are mounted in the lamp housing in radially spaced circular arrays disposed coaxially of the housing centerline, so that the reflected beams of a respective circular array thereof are directed at a predetermined angle of incidence toward the centerline of the lamp housing.

The paraboloidal or ellipsoidal reflector has a relatively large diameter opening in its upper end which is nearly equal in diameter to that of the disc-shaped lamp housing, and is releasably secured by a plurality of clamps or the like coaxially over the lower end of the housing. In its opposite, lower end, the reflector has a smaller opening for accommodating an article or workpiece, or a portion thereof, which is positioned on a worktable or support located beneath the reflector.

THE DRAWINGS

FIG. 1 is a fragmentary sectional view taken generally along the line 1—1 in FIG. 2 looking in the direction of the arrows, and illustrating an objective lens system surrounded by an annular lamp housing containing circular arrays of light sources that direct beams of light downwardly onto the reflecting surface of a paraboloidal mirror that projects coaxially beneath the lamp housing, toward a workpiece which is shown fragmentarily in broken lines as it appears when supported in an opening in the lower end of the mirror;

DETAILED DESCRIPTION OF THE PREFERRED EMBODIMENTS

Figure 1:
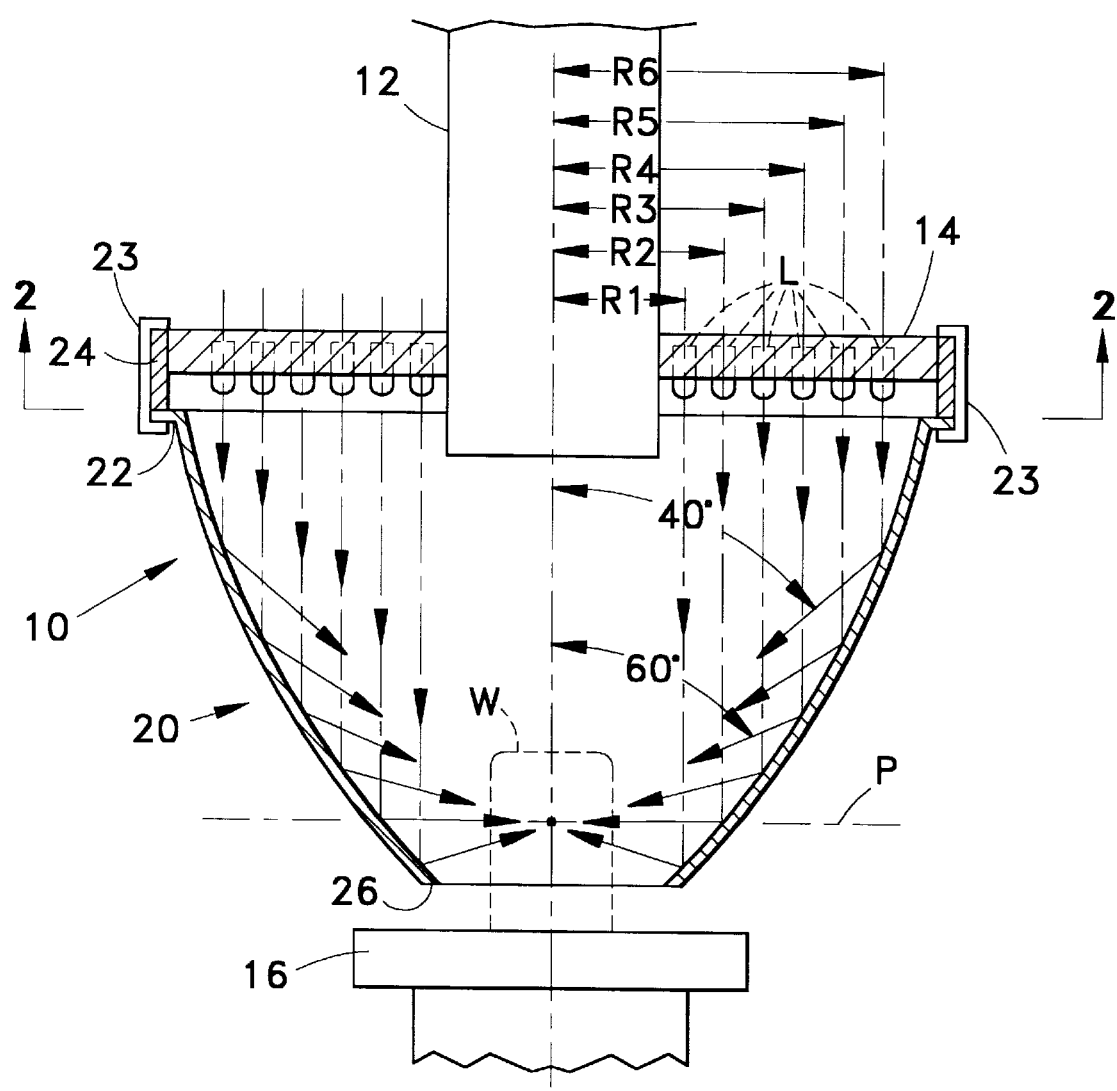

Referring now to the drawings by numerals of reference, and first to FIG. 1, 10 denotes generally a surface illuminator of the type having a cylindrical lens housing 12 containing a conventional objective lens system (not illustrated). Secured to and surrounding the lower end of housing 12 is an annular, generally disc-shaped lamp supporting housing 14, which may be similar in configuration to the correspondingly identified housing in the above-noted U.S. Pat. No. 5,690,417. The surface illuminator 10 is mounted to overlie a work table or support 16 for vertical adjustment toward or away from the table 16, and relative to a workpiece W (broken lines in FIG. 1) which is mounted on the table or support 16.

Removably secured at its larger upper end to, and projecting at its smaller lower end 26 downwardly and coaxially beneath the lamp housing 14 is a concave paraboloidal or ellipsoidal mirror or reflector to, the inner surface of which is the reflective surface. The outer surface of reflector 20 need not be reflective. Around its upper, larger diameter end, the reflector 20 has thereon an integral, circumferential, laterally projecting flange 22, which is removably secured by a plurality of clips or clamps 23 to the underside of an annular clamp or ring 24. Ring 24 is secured coaxially to the outer peripheral surface of the housing 14, and extends for a short distance axially beneath the bottom of housing 14.

Figure 2:
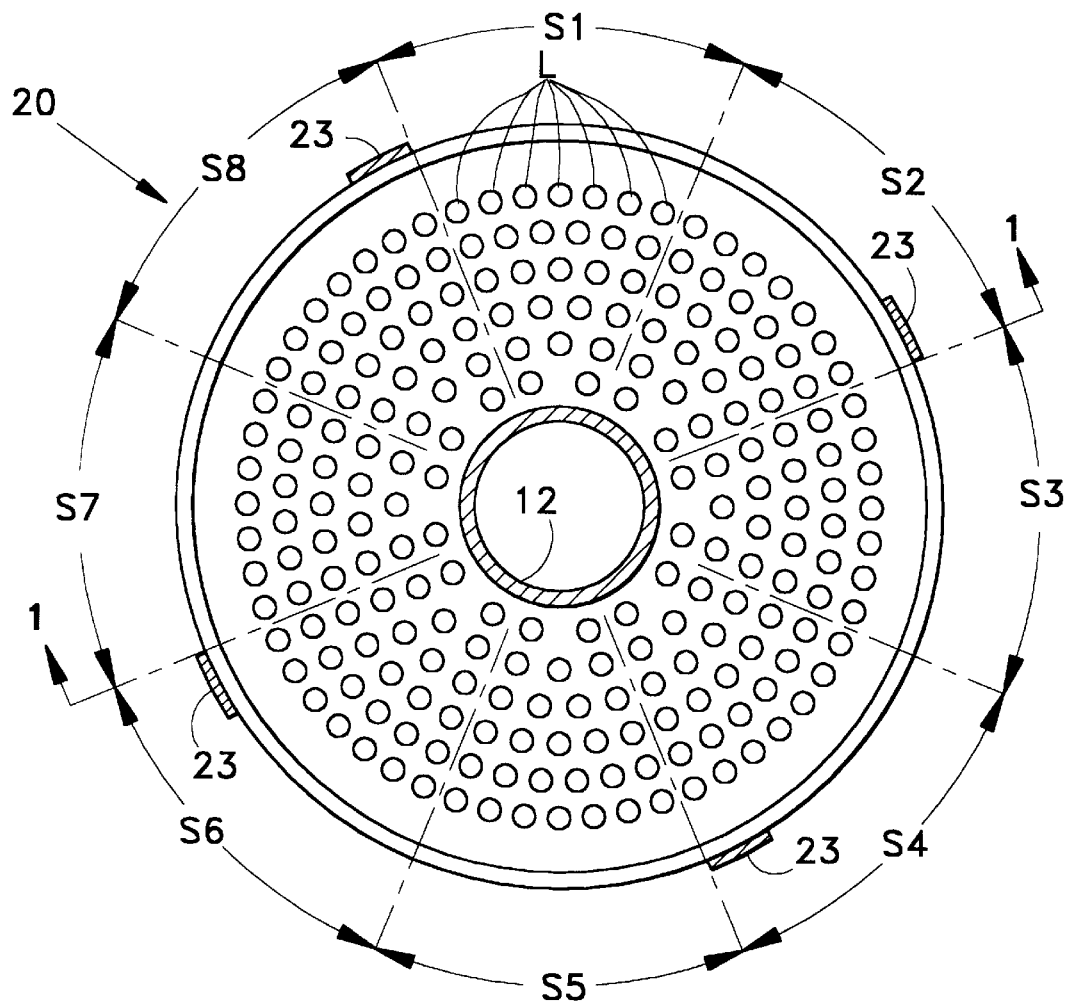
FIG. 2 is a sectional view taken generally along the line 2—2 in FIG. 1 looking in the direction of the arrows.

As shown in FIGS. 1 and 2, housing 14 has mounted therein two hundred sixteen lamps L, which in practice may be collimated light emitting diodes (LED's) of the type sold by Hewlett Packard under the designation HLMA-CHOO/-CLOO. The lamps L shown in FIGS. 1 and 2 herein are secured at their inner ends in housing 14 to extend in spaced, parallel relation to each other, and are arranged in six coaxially disposed, circular arrays with the lamp centerlines of the respective arrays lying on circles radially spaced from the axial centerline of housing 12 at radial distances denoted as R1, R2, R3, R4, R5 and R6. These lamps L are mounted in a manner similar to that of the lamps L shown in FIG. 3 of the above-noted U.S. Pat. No. 5,690,417, except that in the present case six rather than five circular arrays of lamps are mounted in housing 14. When the lamps herein are energized they direct beams of light downwardly along spaced, parallel axes onto the inner, reflective surface of the reflector 20. The lamps L disclosed herein are adapted to be selectively energized by a control system generally similar to that shown in U.S. Pat. No. 5,690,417, and to the extent necessary to understand the control system described hereinafter, the related subject matter disclosed in U.S. Pat. No. 5,690,417 (hereinafter the '417 patent) is incorporated herein by way of reference.

Figure 3:
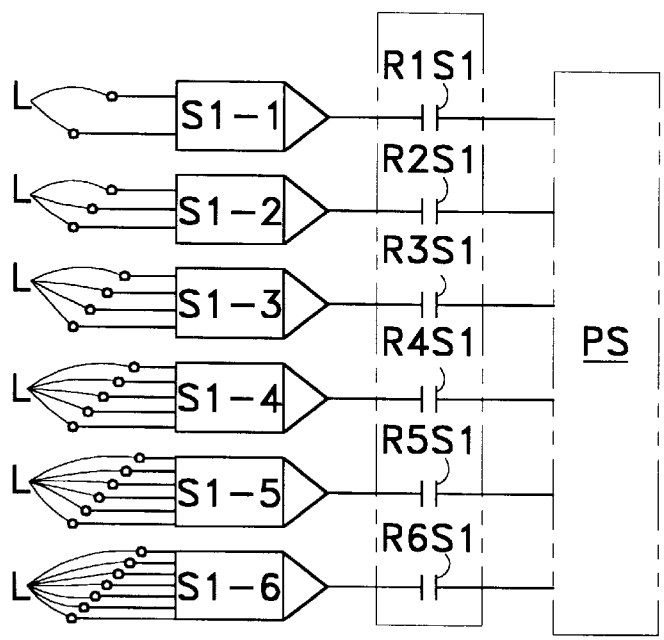
FIG. 3 is a schematic wiring diagram illustrating one manner in which arcuate clusters of the light sources can be selectively energized.

Referring again to FIG. 2, it will be noted, that in addition to being mounted in housing 14 in circular arrays, the lamps L, which are equi-spaced from each other, can be arbitrarily divided into eight equi-angular sectors identified in FIG. 2 as S1 through S8. As in the case of the lamps in the '417 patent, the lamps in each of these sectors are selectively energizable so that illumination from the light sources can be directed selectively from different directions onto a workpiece W that is being inspected. As shown in FIG. 3, for example, the lamps in sector S1 are controlled by six different circuits denoted S1-1 through S1-6, and each of these six different circuits are connected through one of switches R1S1 through R6S1, respectively, to a power supply denoted in FIG. 3 at PS. Whenever any one of the normally-opened switches R1S1 through R6S1 is closed, power supplied to the associated circuit S1-1 through S1-6, thereby energizing the associated lamps L, which in the case of circuit S1-1 will energize the two lamps of sector S1 that are located the distance R1 from the axis of housing 12, and when circuit S1-6 is energized, the seven lamps of sector S1 that are located a distance R6 from the axis of housing 12, would be energized. Although FIG. 3 as explained in connection with only section S1 of the lamps, shown in FIG. 2, it will be understood that seven similar such circuits will be utilized for selectively energizing the lamps in each of the seven remaining sectors S2 through S8.

Figure 4:
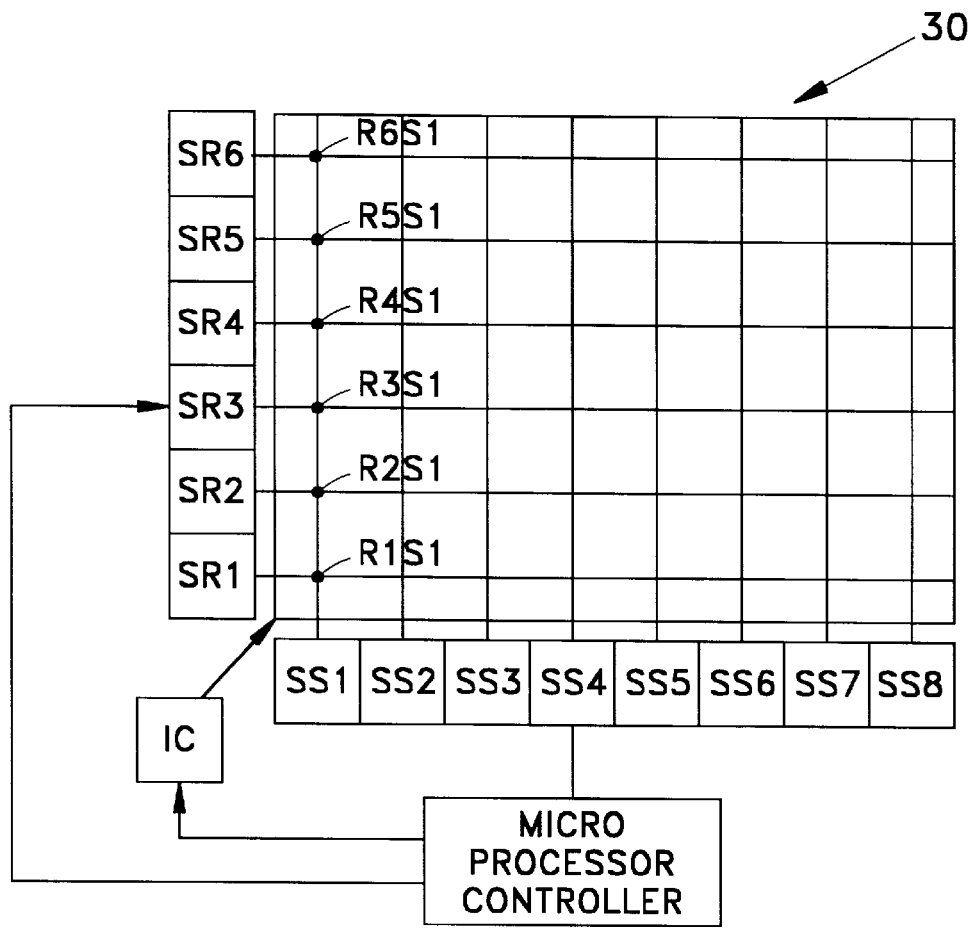
FIG. 4 is a schematic diagram illustrating one manner in which selective illumination of the light sources may be controlled.

In FIG. 4, for example, numeral 30 denotes generally a microprocessor/controller which can be utilized for selectively supplying power to a selected group of lamps in each of the sectors S1 through S8. This controller, which is generally similar to that disclosed in FIG. 6 of the above-noted '417 patent, includes switches SS1 through SS8 for selectively actuating or selecting a particular sector of lamps L, and switches SR1 and SR6 each of which is associated one of the six circular ring of lamps from the radial innermost controlled by SR1 to the radial outermost controlled by switch SR6. Thus, selective closing of one of the switches SS1 through SS8 sends a signal to the switching matrix 30 indicating which sector of lamps had been selected for energization; and then the closing of one or more of the switches SR1 through SR6 will cause corresponding closing of one of the associated switches R1S1 through R6S1, and consequent energization of the lamps associated therewwith. This operation is similar to that effected by the microprocessor controller disclosed in the above-noted '417 patent. Moreover, the circuit denoted at IC in FIG. 4 herein is similar to that described in the above-noted '417 patent, in that the IC circuit can be controlled by the controller of FIG. 4 to function as a global intensity control so that the overall intensity of illumination generated by the lamps L can be controlled, as desired.

From the foregoing, it will be apparent that the present invention provides an improved version of a controller disclosed in U.S. Pat. No. 5,690,417, since the reflector 20, in combination with the lamps L, permits numerous light beams with different angles of incidence to be directed onto the workpiece W that is to be inspected. For example, as shown in FIG. 1, the light emitted by the lamps L in the outermost ring (R6) reflect beams of light having an angle of incidence of approximately 40°, while the angles of incidence increase substantially for the lamps that are in the rings that are radially closer to the housing 12. For example, with respect to the lamps in the ring denoted by R4, their reflected light beams are shown to be directed onto the workpiece W at an angle of incidence of approximately 60°. On the other hand, the angles of incidence for the lamps in the ring R2 are approximately 90°, while for the radially innermost lamps in the ring R1, their reflected beams of light are directed onto the workpiece W at an angle of incidence in excess of 90°. In this embodiment, as shown in FIG. 1, the object plane which is denoted by the line P, lies in a plane normal to the centerline of the reflector 20, and is located above the lower, open end 26 of the reflector 20. With this construction it is possible for the workpiece W to extend through the open, lower end 26 of the reflector 20, and into the center of the reflector, whereby it will be surrounded by illumination reflected from the inner surface of the reflector. With this construction, the light beams which are reflected onto the workpiece W at an angle greater than 90°, in essence direct illumination slightly upwardly from beneath the object plane, which in certain instances may be particularly suitable for inspecting a workpiece W of unusual shape.

Further than this, it is to be understood that the surface illuminator 10 and/or the support 16 are mounted for axial movement relative to each other thereby to selectively increase or decrease the distance between the upper surface of the support 16, and the open, lower end 26 of the reflector. Also, it is to be understood that the portion of the paraboloid which is removed to form the opened, lower end 26 thereof, can be increased, if desired, thereby to increase the size of the circular opening formed in the lower end of the reflector. In practice this could raise the lower, open end of the reflector 20 above the object plane P so as to provide a greater working distance or clearance by virtue of providing an opening of larger diameter in the lower end of the reflector 20.

From the foregoing it will be apparent that the present invention provides a relatively simple and inexpensive means for producing a high-incidence programmable surface illuminator by utilizing, in combination with circular arrays of collimated light sources, a removable paraboloidal reflector for directing collimated beams of light onto a workpiece that is to be inspected, and at angles of incidence that range from around from about 45° to beyond 90°. The reflector 20 may, if desired, be secured to the underside of housing 14 by conventional means other than by clamps 23, for example by a magnetic coupling or a threaded connection. Moreover, while this invention has been illustrated and described in detail with only certain embodiments thereof, it will be apparent that this application is intended to cover any such modifications as may fall within the scope of one skilled in the art, or within the scope of the appended claims.

What is claimed is:

1. A high-incidence programmable surface illuminator for inspecting objects, comprising
   a lens housing having therethrough an axial bore containing a lens system for projecting through said bore the image of an illuminated object located in a predetermined position beyond one end of said lens housing,
   a lamp housing surrounding said lens housing and having in one end thereof a central opening registering coaxially with said bore,
   a plurality of collimated light sources mounted in said lamp housing in spaced relation to each other and operable to direct through said central opening and toward said object a plurality of spaced, parallel, collimated light beams arranged in radially spaced circular arrays disposed coaxially of said bore, and
   a hollow reflector interposed between said lamp housing and said object, said reflector having in one end thereof a first opening seated coaxially around said central opening in zo said lamp housing, and having in its opposite end a second opening disposed coaxially of said first opening and confronting upon said object,
   said reflector having formed therein an internal paraboloidal shaped reflective surface extending coaxially between said first and second openings in said reflector, and operative to reflect light from said collimated light beams toward said object.

2. A high-incidence programmable surface illuminator as defined in claim 1, wherein said reflective surface is operative to direct reflected light from said beams toward a focal point located in an object plane extending normal to the common axis of said first and second openings, and positioned adjacent said second opening in said reflector.

3. A high-incidence programmable surface illuminator as defined in claim 2, wherein a portion of said object projects into said reflector through said second opening therein and beyond said object plane.

4. A high-incidence programmable surface illuminator as defined in claim 3, wherein said reflective surface is operative to direct reflected beams of light onto said portion of said object at angles of incidence in the range of 40° to in excess of 90°.

5. A high-incidence programmable surface illuminator as defined in claim 1, including means releasably securing said one end of said reflector to said one end of said lamp housing around said central opening thereof.

6. A high-incidence programmable surface illuminator as defined in claim 1, including control means for selectively energizing said light sources to control the amount and orientation of the light reflected by said reflective surface toward said object.

7. A high-incidence programmable surface illuminator as defined in claim 6, wherein said light sources are disposed in radially spaced circular arrays surrounding said lens housing, and
   said control means includes a plurality of electrical circuits each of which controls a predetermined number of adjacent light sources in each of said arrays thereof, each of said circuits including switch means operable selectively to energize in one or more of said arrays of light sources said adjacent number of light sources controlled thereby, and
   said predetermined number of adjacent light sources in each array thereof controlled by a respective circuit increasing progressively from a minimum number for the radial innermost of said arrays thereof to a maximum number for the radial outermost of said arrays thereof.

8. A high-incidence programmable surface illuminator as defined in claim 1, wherein said reflective surface is operative to reflect the circular arrays of collimated light beams toward said object at respectively different angles of incidence.

9. A high-incidence programmable surface illuminator as defined in claim 8, wherein said angles of incidence are in the range of 40° to in excess of 90°.

10. A high-incidence programmable surface illminator as defined in claim 1, wherein said paraboloidal shaped surface of said reflector directs reflected light from said beams toward a focal point located intermediate the ends of said reflector on the common axis of said first and second opening.

11. In a surface illuminator for inspecting objects including a lens housing having therethrough an axial bore containing a lens system for projecting through said bore the image of an illuminated object located in a predetermined position beyond one end of said lens housing, and a lamp housing surrounding said lens housing and having therein a plurality of collimated light sources operable to direct through an opening in said lamp housing, and toward said object, a plurality of spaced, parallel, collimated light beams arranged in radially spaced circular arrays disposed coaxially of said bore, the improvement comprising,
   a hollow reflector interposed between said lamp housing and said object, said reflector having in one end thereof a first opening seated coaxially around said opening in said lamp housing, and having in its opposite end a second opening disposed coaxially of said first opening and confronting upon said object, said reflector having formed therein an internal ellipsoidal shaped reflective surface extending coaxially between
   said first and second openings in said reflector, and operative to reflect light from said collimated light beams toward said object.

12. In a surface illuminator as defined in claim 11, wherein said reflective surface is operative to direct reflected light from said beams toward a focal point located in an object plane extending normal to the common axis of said first and second openings, and positioned adjacent said second opening in said reflector.

13. In a surface illuminator as defined in claim 11, wherein a portion of said object projects into said reflector through said second opening therein and beyond said object plane.

14. In a surface illuminator as defined in claim 13, wherein said reflective surface is operative to direct reflected beams of light onto said portion of said object at angles of incidence in the range of 40° to in excess of 90°.

* * * * *